US00PP17674P3

(12) United States Plant Patent
Olesen

(10) Patent No.: US PP17,674 P3
(45) Date of Patent: May 1, 2007

(54) MINIATURE ROSE PLANT NAMED 'POULPAH034'

(50) Latin Name: ***Rosa* hybrid**
Varietal Denomination: Poulpah034

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 18 days.

(21) Appl. No.: 11/240,012

(22) Filed: Sep. 29, 2005

(65) Prior Publication Data

US 2007/0074318 P1 Mar. 29, 2007

(51) Int. Cl.
*A01H 5/00* (2006.01)

(52) U.S. Cl. ..... Plt./119

(58) Field of Classification Search ..... Plt./119, Plt./118, 121, 116

See application file for complete search history.

*Primary Examiner*—Kent Bell
*Assistant Examiner*—June Hwu

(57) ABSTRACT

A new miniature rose plant that has abundant, light pink flowers with pale orange hues and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa hybrid.*
Variety denomination: 'Poulpah034'.

SUMMARY OF THE INVENTION

The present discovery constitutes a new and distinct variety of compact floribunda miniature rose plant which was discovered in a cultivated area. The new rose variety resulted from a naturally occurring mutation of unknown causation on a branch of 'Poulac015', described and illustrated in U.S. Plant Pat. No. 15,171. The resulting mutation was selected and evaluations were conducted on the resulting rose plants in a controlled environment.

The rose plant of the present discovery has a unique combination of characteristics which are outstanding in the new variety and which distinguish it from the original rose as well as all other varieties which we are aware of. For example, the general tonality of flower color for the original rose, 'Poulac015', is described as being Red-Purple Group 63B to 57C. The general tonality of flower color for the claimed plant 'Poulpah034' is described as being Red 49 D becoming Orange 27 D as flowers mature. Additionally, the bloom diameter for the plant variety 'Poulpah034' is greater than the original rose, 'Poulac015'.

The objective of the selection of this rose variety for commercial culture was to create a new and distinct variety with unique qualities, such as:

1. Uniform and abundant light pink flowers with pale orange hues;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah034' from all other varieties of which we are aware.

Asexual reproduction of 'Poulpah034' by vegetative cuttings was first done by Mogens N. Olesen in Fredensborg, Denmark, in July of 1999. This initial and other subsequent propagations have demonstrated that the characteristics of 'Poulpah034' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah034'. Specifically illustrated in the drawing:

FIG. 1.1; Flower buds at various stages of development;

FIG. 1.2; Open flowers;

FIG. 1.3; Open flower attached to stem, showing leaves and flower buds;

FIG. 1.4; Petals, detached;

FIG. 1.5; Mature leaves;

FIG. 1.6; Juvenile leaves;

FIG. 1.7; Sepals, receptacle, and pedicel;

FIG. 1.8; Bare stem.

DETAILED DESCRIPTION OF THE VARIETY

The following is a description of 'Poulpah034', as observed in its growth in a glasshouse located in Fredensborg, Denmark. Observed plants are 4 months of age and were cultivated in 12 cm pots. Color references are made using The Royal Horticultural Society (London, England) Colour Chart, 2001, except where common terms of color are used.

For a comparison, several physical characteristics of the rose variety 'Poulpah026', described and illustrated in U.S. Plant Pat. No. 16,577 are compared to 'Poulpah034' in Chart 1.

CHART 1

| | 'Poulpah034' | 'Poulpah026' |
|---|---|---|
| Petalage: | 80 to 85 | 50 to 55 |
| General tonality of flower color: | Red 49 D becoming Orange 27 B to 27D as flowers mature | Red 38 D with intonations of Orange 29 B |
| Flower bud length: | 18 to 25 mm | 33 mm |

FLOWER AND FLOWER BUD

Blooming habit: Continuous.

Flower bud:

*Size.*—Upon opening, 18 to 25 mm in length from base of receptacle to end of bud. 11 to 15 mm in diameter.

*Bud form.*—Urceolate.

*Bud color.*—As sepals unfold, petals are Orange-Red Group 31 C to Orange Group 29 B with intonations of Orange-Red Group N34C.

*Sepals.*—Upper Surface: Color: Yellow-Green Group 146B Texture: Smooth. Sparsely pubescent. Lower Surface: Color: Yellow Green Group 146 A. Texture: Somewhat rough with many stipitate glands. Shape: Apex: Cirrhose. Base: Flat at union with receptacle. Margins: Margins have weak foliaceous appendages on three of the five sepals. Stipitate glands are abundant. Size: 30 mm long by 6 mm wide.

*Receptacle.*—Surface Texture: Smooth. Shape: Urn-shaped. Size: 5 mm in height by 7 mm wide. Color: Yellow Green Group 144 A. Anthocyanin: None observed.

*Pedicel.*—Surface: Slightly rough with stipitate glands. Stipitate glands release spicy scent when touched. Length: 25 mm average length. Diameter: 3 mm. Color: Yellow Green Group 144 A. Strength: Strong, erect.

*Borne.*—Small clusters of 3 to 4 flower buds per flowering stem on average. Nearest inflorescence type is a panicle.

Flower bloom:

*Fragrance.*—Moderate floral scent.

*Duration.*—As a pot plant, flowers last from 14 to 18 days. Petals do not fall cleanly away from plant after flowers have matured.

*Size.*—Flower diameter is 70 to 80 mm when open. Flower depth is normally 30 mm.

*Form.*—General shape is a semi cupped quartered-rosette, with many overlapping petals packed tightly into quarter sections.

*Shape of flower, side view.*—Upon opening, the upper portion is flat. The lower portion is concave. After opening, the upper portion is flat and the lower portion is concave.

Petalage: There are normally 80 to 85 petals under normal conditions, 15 to 20 of which are considered petaloids.

Color:

*Upon opening, petals.*—Outermost petals: Upper Surface: Red Group 36 D to Red Group 49 D. Lower Surface: Red Group 36 D to Red Group 49 D with an overlay the color of Red-Purple Group 62 B. Innermost petals: Upper Surface: Red Group 36 D. Lower Surface: Red Group 36 D to Red Group 49 D with an overlay the color of Red-Purple Group 62 B.

*Upon opening, basal petal spots.*—Upper Surface: Pale, Yellow Group 13 D. Lower Surface: No distinctive coloration.

*After opening, petals.*—Outermost petals: Upper Surface: Orange Group 27 C to Red Group 36 D. Lower Surface: Red Group 36 C with an overlay the color of Red-Purple Group 62 B. Innermost petals: Upper Surface: Yellow-Orange Group 18 D with light intonations of Red Group 38 D. Lower Surface: Yellow Orange Group 19 C to 19 D with a light overlay the color of Red Group 36 A.

*After opening, basal petal spots.*—Upper Surface: Yellow Group 8 C. Lower Surface: Yellow Group 8 D.

General tonality: On open flower the tonality is initially Red Group 49 D. As flowers mature, the color changes to Orange Group 27 B to 27D.

Petals:

*Petal reflex.*—Slightly.

*Petal margin.*—Entire and uniform with weak undulations of margin.

*Shape.*—Generally broad elliptical. Base: Obtuse. Apex: Rounded.

*Size.*—Outer petals are normally 35 mm in length by 35 mm wide. Inner petals are 24 mm long by 23 mm wide.

*Texture.*—Smooth.

*Thickness.*—Average.

Petaloids:

*Quantity.*—Normally, there are 15 to 20.

*Size.*—12 mm long; 10 mm wide.

*Shape.*—Irregular. Apex and base are generally acute.

*Color.*—Upper Surface: Yellow-Orange Group 18 D with light intonations of Red Group 38 D. Lower Surface: Yellow Orange Group 19 C to 19 D with a light overlay the color of Red Group 36 A.

Reproductive organs:

*Pollen.*—None observed.

*Anthers.*—Size: 2.5 mm long. Color: Yellow-Orange Group 22 A. Quantity: 40 to 45.

*Filaments.*—Color: Red Group 39 B. Length: 5 to 8 mm.

*Pistils.*—Length: 3 mm long. Quantity: 35 to 40.

*Stigmas.*—Inferior in height, relative to the length of the filaments and the height of the anthers. Color: Greyed-Yellow Group 160 D.

*Styles.*—Color: White Group 155B and occasionally with intonations of Red Group 42 A.

*Seed formation.*—Not observed.

PLANT

Plant growth: Compact, upright and bushy. When grown as a 12 cm pot plant on its own roots, the average height of the plant itself is 30 to 34 cm and the average width is 20 cm.

Stems:

*Color.*—Young wood: Yellow-Green Group 144 B. Older wood: Yellow-Green Group 146 A.

*Internodal distance.*—25 to 33 mm on average.

*Length of stems.*—From the base of the stem to the flowering portion, stems are 15 to 20 cm in length.

*Diameter of stems.*—Normally 3 to 3.5 mm.

*Surface texture.*—Young wood: Smooth. Older wood: Smooth.

Thorns:

*Incidence.*—0 to 1 per 10 cm of stem.

*Size.*—Average length: 4 mm.

*Color.*—Juvenile and mature thorns are Greyed-Yellow Group 160 C to Yellow-Green Group 144B.

*Shape.*—Upper and lower side are flat.

Plant foliage: Normal number of leaflets on normal leaves in middle of the stem: 5 leaflets.

*Compound leaf size.*—75 to 85 mm (l)×58 to 65 mm (w).

*Quantity.*—4 leaves per 10 cm of stem.

*Color.*—

*Juvenile foliage.*—Upper side is Yellow-Green Group 144 A with light anthocyanic intonations of Greyed-Red Group 181 A found on the margins. Lower side is Yellow-Green Group 146 C.

*Mature foliage.*—Upper surface is Yellow-Green Group 147 A. Lower surface is Yellow-Green Group 147 B.

Plant leaves and leaflets:

*Stipules.*—Size: 10 mm to 14 mm in length. Shape: Linear, slightly broad based with outward extending apecies. Margins: Serrated with stipitate glands. Color: Yellow-Green Group 146 B.

*Petiole.*—Length: 15 mm in length with a normal diameter of 1 mm. Color: Upper surface is Yellow-Green Group 146 B. Lower surface is Yellow-Green Group 146 C. Anthocyanin: Pale intonations of Greyed-Red Group 178 A. Margin: Few stipitate glands observed. Underneath: Few small prickles observed.

*Rachis.*—Size: 22 to 30 mm in length. Color: Yellow-Green Group 146 B with pale intonations of Greyed-Red Group 178 A on the upper surface. Lower surface is Yellow-Green Group 146 C. Upper Surface: Few small prickles located mid-way between leaflets.

*Leaflet.*—Size: 35 to 45 mm in length by 22 to 28 mm wide. Margin: Doubly serrated. General Shape: Ovate. Apex Shape: Acute. Base Shape: Obtuse. Texture: Smooth. Thickness: Average. Arrangement: Odd pinnate. Venation: Reticulate. Leaf Gloss: Very glossy.

Disease resistance: Average resistance to powdery and downy mildew, black spot, and Botrytis under normal glasshouse growing conditions in Fredensborg, Denmark.

It is claimed:

1. A new and distinct variety of rose plant of the miniature class named 'Poulpah034', substantially as illustrated and described herein, due to its abundant, light pink flowers with pale orange hues, vigorous growth, compact habit, suitability for production from softwood cuttings in pots, and durable flowers and foliage that make the variety suitable for distribution in the floral industry.

* * * * *

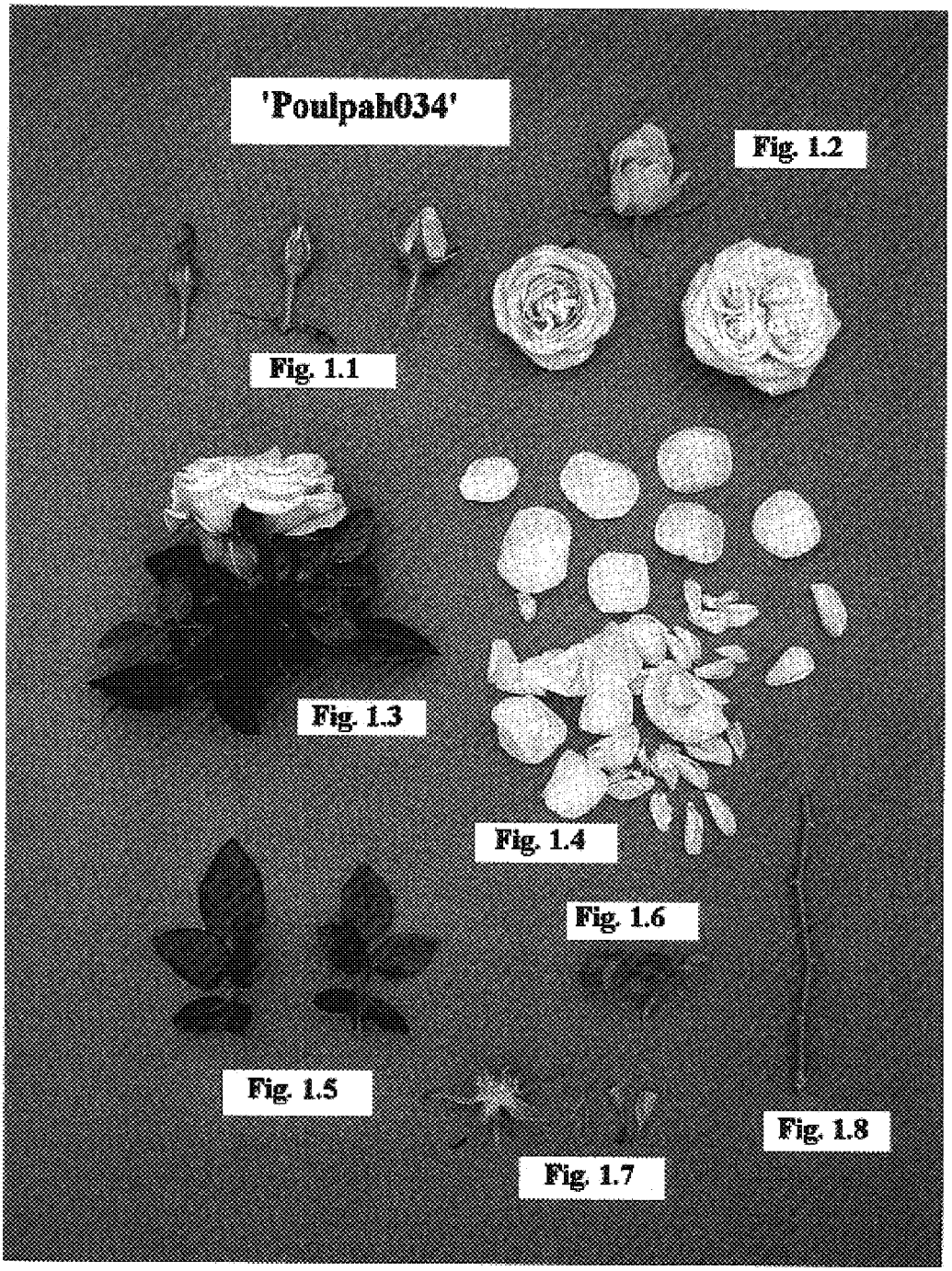
'Poulpah034'
Fig. 1.2
Fig. 1.1
Fig. 1.3
Fig. 1.4
Fig. 1.6
Fig. 1.5
Fig. 1.8
Fig. 1.7